Figure 5:
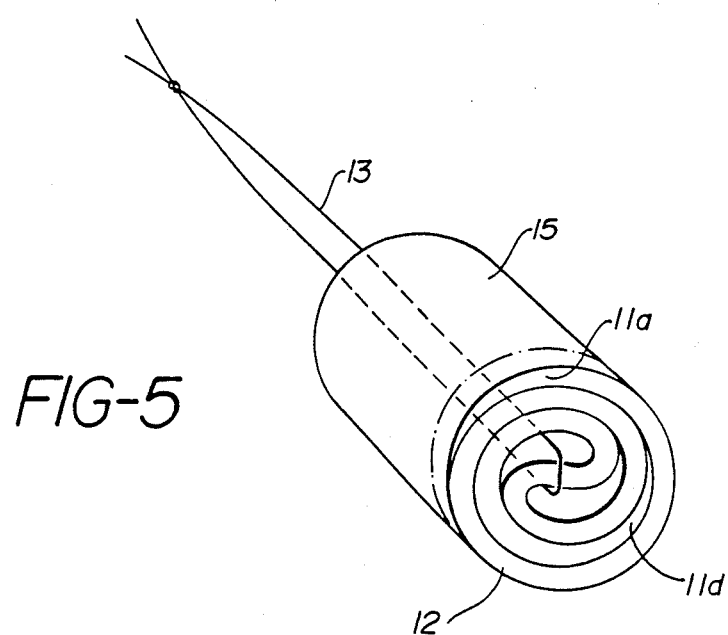

United States Patent [19]

Friese

[11] Patent Number: 4,863,450
[45] Date of Patent: Sep. 5, 1989

[54] FEMININE HYGIENE TAMPON AND METHOD AND APPARATUS FOR MAKING SAME

[75] Inventor: Axel Friese, Wuppertal, Fed. Rep. of Germany

[73] Assignee: Johnson & Johnson GmbH, Dusseldorf, Fed. Rep. of Germany

[21] Appl. No.: 110,901

[22] Filed: Oct. 20, 1987

Related U.S. Application Data

[63] Continuation of Ser. No. 768,098, Aug. 5, 1985.

[30] Foreign Application Priority Data

Dec. 30, 1983 [DE] Fed. Rep. of Germany ....... 3347649

[51] Int. Cl.⁴ ............................................. A61F 13/16
[52] U.S. Cl. .................................... 604/370; 604/379
[58] Field of Search .............. 604/366, 358, 367, 370, 604/372, 373, 374, 379, 377, 385.1, 904

[56] References Cited

U.S. PATENT DOCUMENTS

| | | | |
|---|---|---|---|
| 2,099,931 | 11/1937 | Fourness | 604/904 |
| 3,359,981 | 12/1967 | Hochstrasser | 604/374 |
| 3,523,535 | 8/1970 | Croon et al. | 604/904 |
| 3,683,912 | 8/1972 | Olson et al. | |
| 3,854,481 | 12/1974 | Messing | 604/904 |
| 4,069,822 | 1/1978 | Buell | 604/366 |
| 4,305,391 | 12/1981 | Jackson | |
| 4,355,066 | 10/1982 | Newman | 604/366 |
| 4,552,795 | 11/1985 | Hansen et al. | 604/358 |

*Primary Examiner*—C. Fred Rosenbaum
*Assistant Examiner*—Denise Whelton
*Attorney, Agent, or Firm*—Joseph F. Shirtz

[57] ABSTRACT

The invention relates to a tampon (10), to the essentially cylindrical circumferential surface of which a liquid-permeable, thermoplastic material is fastened, with the application of pressure and heat. The dome-like constriction (10b) at the introduction end (10a) and the withdrawal end (10c) of the tampon (10) remain free of the liquid-permeable, thermoplastic material. The fastening of the liquid-permeable material to the outer surface of the absorbent material of the tampon (10), which consists of a nonwoven ribbon section rolled up on itself and pressed radially to give the final form of the tampon (10), guarantees that the high absorbency of the nonwoven fibre material, based on capillary action, continues through the liquid-permeable, thermoplastic material onto its outside. In addition, the liquid-permeable material offers protection against fibres becoming detached and makes it easier to introduce the tampon into and remove it from the body cavity.

10 Claims, 5 Drawing Sheets

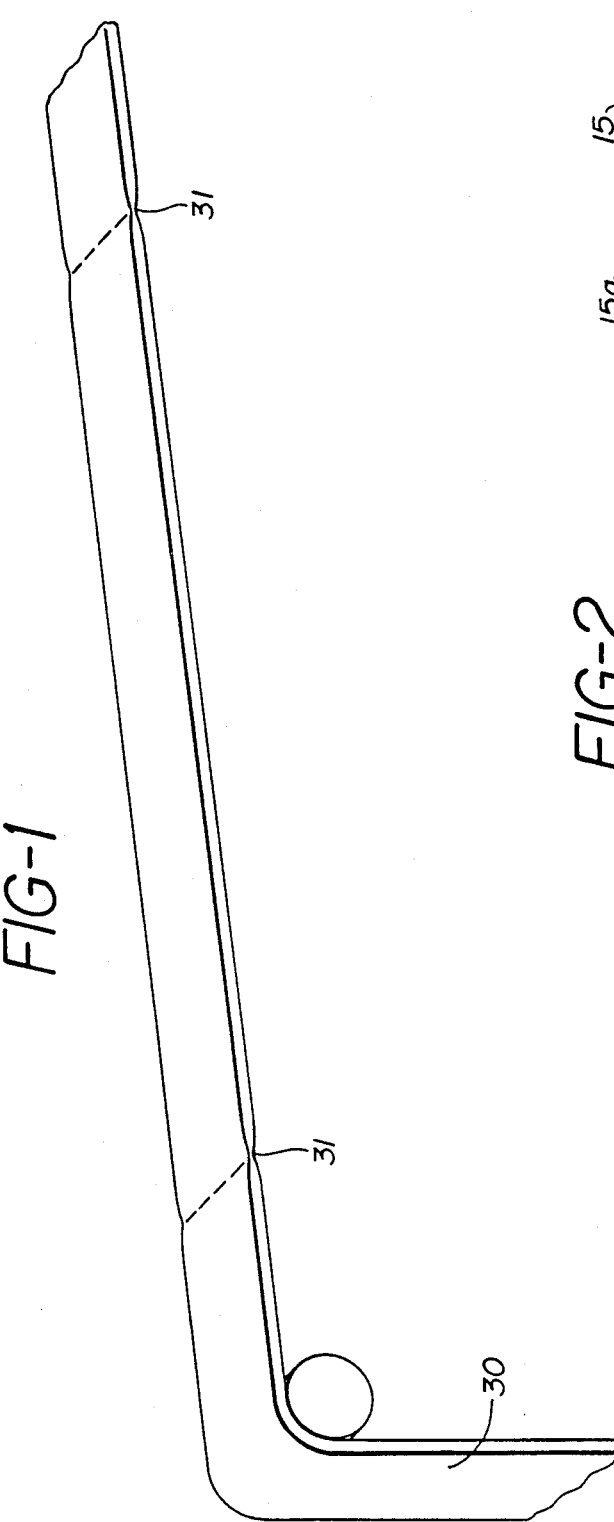
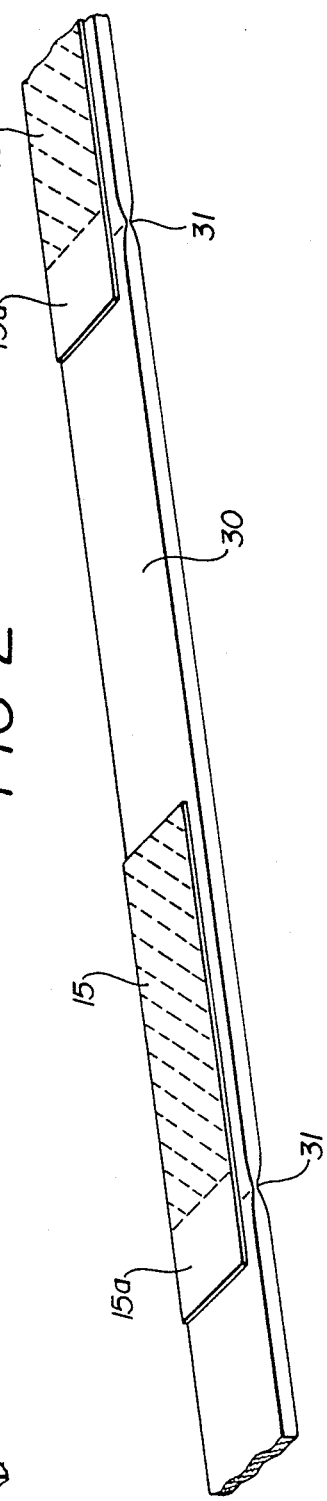

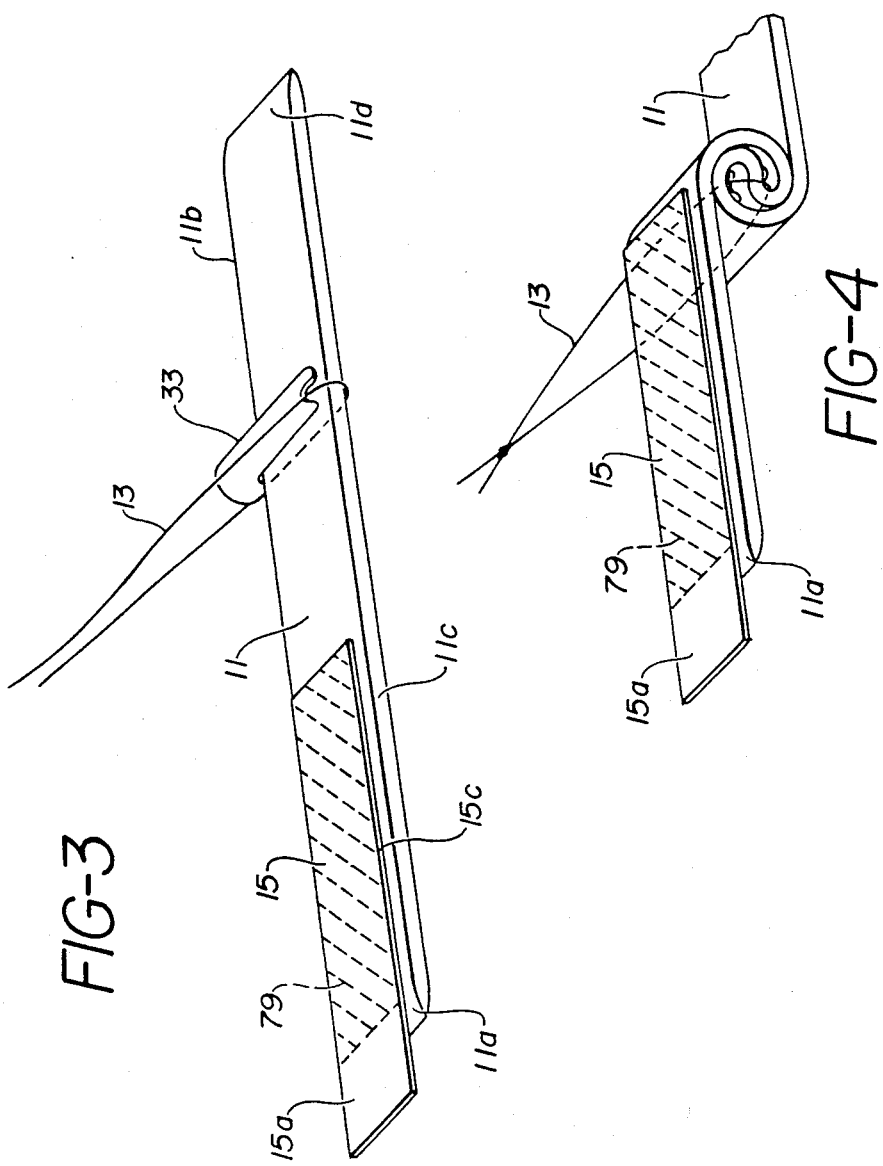

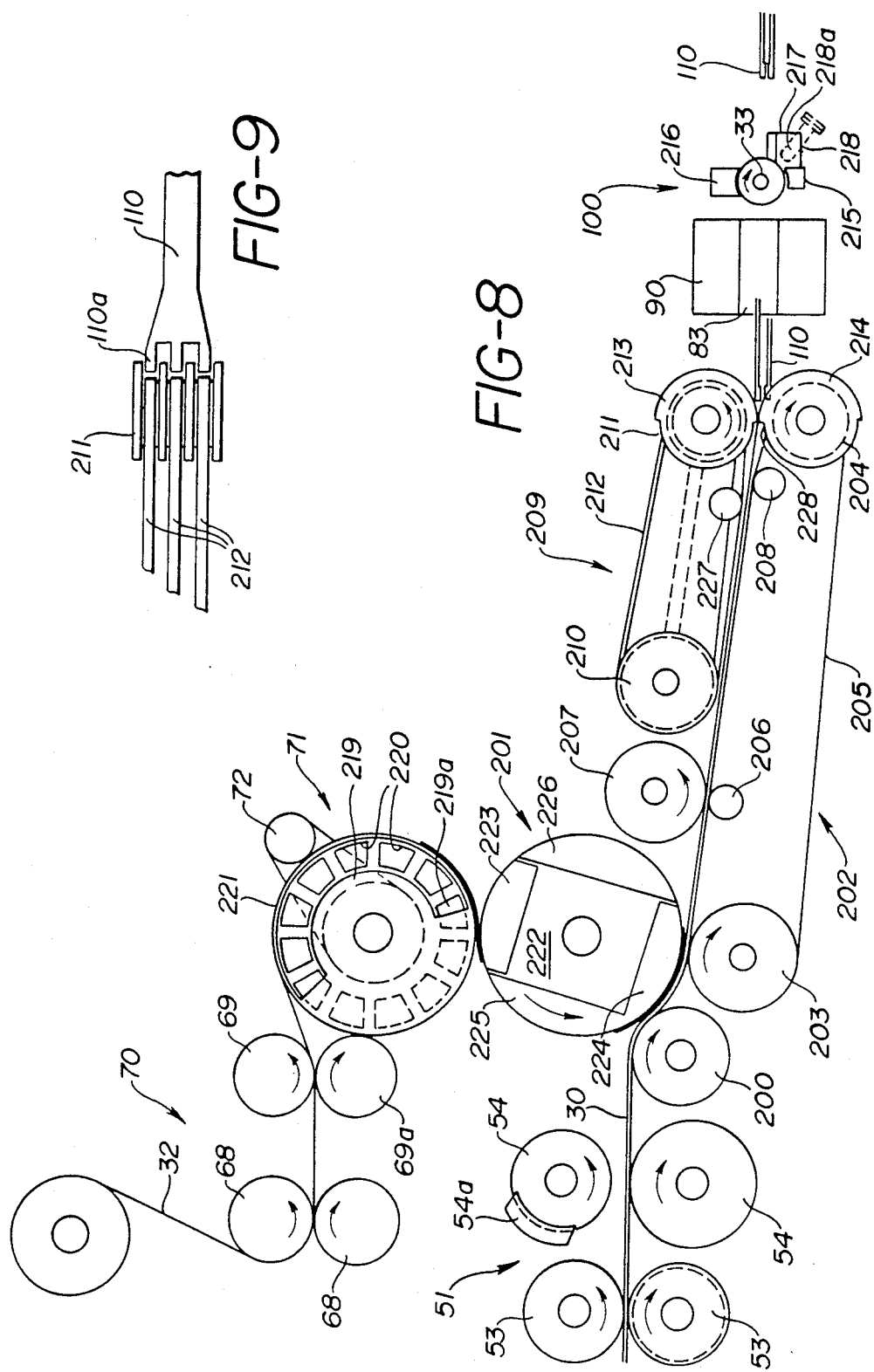

FEMININE HYGIENE TAMPON AND METHOD AND APPARATUS FOR MAKING SAME

This is a continuation of application Ser. No. 786,098, filed Aug. 5, 1985.

The invention relates to a tampon for female hygiene, consisting of a section of specific length of a nonwoven ribbon which is composed of randomly laid natural and/or synthetic fibres and which has a width corresponding approximately to the length of the tampon, and of a strip section fixed to one end of the nonwoven ribbon section, of a liquid-permeable, at least partially thermoplastic material, the nonwoven ribbon section being wound essentially upon itself to give a tampon blank which is provided with a withdrawal cord and upon the circumference of which the strip section is rolled and which is pressed essentially radially to give the final form of the tampon.

Tampons of the abovementioned type and machines for producing them are known, for example, from German Patent Specifications 915, 382, 1,491,162, 1,491,200, 1,938,942 and 2,135,495. Tampons of this type have proved outstanding in practice, because they have not only a high suction capacity, but also excellent expandability when the tampon is wetted with liquid, giving the user reliable menstruation protection. Along with these properties, the tampon also has the technical advantage that it can be manufactured in mass production, that is to say in large quantities with a high uniform quality.

Swiss Patent Specification 635,508 makes known a tampon for female hygiene, which consists of a rolled-up and pressed nonwoven ribbon section and which is to be provided in a special way with a withdrawal cord. Since, depending on specific physiological preconditions, it is not possible completely to prevent fibres from being detached during the use of such tampons, when the tampon is introduced into, but especially removed from the body cavity, this tampon is surrounded with a wrapping consisting, for example, of nonwoven material. When this tampon is produced, a section of the wrapping material, which is made substantially wider than the nonwoven ribbon section, is fastened to one end of the nonwoven ribbon section consisting of absorbent material. After the nonwoven ribbon section has been rolled up, together with the section forming the wrapping, the wrapping edges project respectively beyond the two ends of the tampon blank, so that these cylindrical wrapping ends have to be inserted in the central gap between the layers of absorbent material of the tampon blank before the latter is pressed to give the final form of the tampon. This operation of wrapping the tampon loosely with the exception of the fastening of the wrapping section to one end of the nonwoven ribbon section results in the danger that a gap will form between the wrapping and the tampon material, so that the instant absorption of any liquid, desired when the tampon is used, is impeded because the capillary action of the fibrous tampon material, essential for absorption, cannot continue effectively through the wrapping material up to the outside of the wrapping material. This impairs the suction capacity and consequently the rapid expansion of the tampon, even though these play a decisive part in the protective action of the tampon. Furthermore, production problems arise when the ends of the wrapping material, which project in the manner of a sleeve beyond the ends of the tampon material of the tampon blank, are inserted into the end faces of the tampon blank, since this is an operation which is at least relatively difficult to carry out and which will necessarily be detrimental to the production speed and consequently increase the production costs of the known tampon.

U.S. Patent Specification 3,523,535 makes known a tampon for medical or surgical purposes. This tampon is produced when an air-placed layer of wood-pulp fibres, six to eight mm thick, is applied to the top side of a continuous liquid-permeable sheet of thermoplastic nonwoven material. The sheet consisting of the two layers is then drawn through a form tool, in which the longitudinal edges of the sheet consisting of the two layers are laid over one another at the top to form a cylinder and are joined to one another under the effect of heat and pressure. The longitudinally extending cylindrical material is subsequently cut to the desired tampon length. Tampons of this type are unsuitable for female hygiene, and consequently it has not been possible to use them successfully in practice for this purpose. The reasons for this are, among other things, that this known tampon cannot expand. This is because the slight radial compression of the wood-pulp fibres takes place in the drawing die, before the ends of the nonwoven material, which overlap in the circumferential direction of the cylindrical strand, are welded to one another. The wood-pulp fibres are largely inelastic and do not give the tampon the necessary stability or bending strength which is required to allow the tampon to be introduced easily into the body cavity. When wetted with liquid, the wood-pulp fibres disintegrate, so that the tampon is not dimensionally stable.

The object on which the invention is based is to improve further a tampon of the known type mentioned in the introduction, by protecting it against fibre fluff becoming detached and giving it a surface structure which allows the tampon to be introduced gently and smoothly into the body cavity, without the absorbency, suction capacity and the important expansibility of the tampon being impaired. At the same time, despite this improvement, it will also be possible to manufacture the tampon economically in mass production, whilst ensuring high quality.

The invention achieves this object due to the fact that the liquid-permeable, thermoplastic strip section is bonded by heat-sealing to the outside of the nonwoven ribbon section over a length which approximately corresponds to the length of the circumference of the tampon blank, and the outer end of the strip section, which projects beyond the end of the nonwoven ribbon section, is welded to the outside of part of the strip section sealed to the nonwoven ribbon section. Advantageously, the strip section is made narrower than the width of the nonwoven ribbon section, so that the nonwoven ribbon material present exclusively at the introduction end can be shaped into a constriction and can be available for the immediate absorption of liquid. The nonwoven material of the strip section is advantageously composed of a bi-component fibre, the sheathing of which has a lower melting point than the fibre core, so that, even at a high manufacturing speed necessary for mass production, on the one hand sealing of the strip section to the nonwoven ribbon section is achieved reliably, but on the other hand the structure of the nonwoven strip section is maintained.

The tampon according to the invention can advantageously be produced by means of a process in which a length section of a liquid-permeable, thermoplastic nonwoven strip of material is welded to the outside of the rear end of a nonwoven ribbon section of specific length, the width of the nonwoven ribbon section approximately corresponding to the length of the tampon, whereupon the nonwoven ribbon section is provided with a withdrawal cord and rolled up on itself to form a tampon blank, so that the strip section extends over the circumference of the tampon blank which is subsequently pressed to give the final form of the tampon. To produce the tampon according to the invention, such a process is developed so as to ensure that the thermoplastic strip section is sealed to the nonwoven ribbon section over a length approximately corresponding to the circumferential length of the tampon blank and, after the nonwoven ribbon section has been rolled up to give the tampon blank, the unsealed end projecting beyond the nonwoven ribbon section is welded to the strip section with the application of heat and pressure.

An apparatus for producing the tampon according to the invention consists appropriately of the following devices arranged in series in the direction of processing:

A stock roll for a continuous nonwoven ribbon of natural and/or synthetic fibres;
- a weakening station for the nonwoven ribbon;
- a transport device for the nonwoven ribbon;
- a nonwoven ribbon-severing device for the continuous severing of nonwoven ribbon sections;
- a withdrawal cord-attaching and -knotting device;
- a winding station for rolling up the nonwoven ribbon section to form a tampon blank;
- transport and severing tongs which can be moved to and fro approximately in the transport plane of the nonwoven ribbon and which are intended for severing one nonwoven ribbon section each time; and
- a device for transferring the tampon blank to a press, in which the tampon blank can be pressed substantially radially to give the final form of the tampon, and a device for forming the introduction end of the tampon.

For producing the tampon according to the invention, an apparatus of this type is characterised in that a stock roll for a continuous strip of nonwoven liquid-permeable thermosplastic material is provided, this stock roll being followed by a cutting station for largely severing the continuous strip into sections of specific length, after which a separation and transfer device for the strip sections is arranged, which is followed by a sealing station for sealing the thermoplastic strip section onto the outside of the nonwoven ribbon, downstream of which a device for continuously transporting the nonwoven ribbon with the strip section sealed to it to a nonwoven ribbon-severing device is provided, and in that the winding station is associated with a heatable welding and smoothing device for pressing the end, extending freely and unsealed beyond the rear end of the nonwoven ribbon section, of the strip section against the strip section sealed onto the nonwoven ribbon section.

Because the liquid-permeable thermoplastic material is fastened to the nonwoven ribbon, no gap can form between the nonwoven ribbon section and the strip section. At the same time, the expandability and the suction capacity of the pressed tampon are fully preserved. The thermoplastic material on the circumference of the tampon opposes substantially less resistance to the introduction of the tampon into the body cavity so that the user finds introduction more comfortable and easier, whilst at the same time there is no possibility that fibres will become detached when the tampon is introduced and removed. The firm bond between the thermoplastic strip section and the nonwoven ribbon section guarantees perfect, smooth contouring of the outside of the tampon, and this also contributes to increased comfort when the tampon is introduced. At the same time it has been shown surprisingly that, even at very high production speeds, it is possible to seal the thermoplastic strip section to the nonwoven ribbon perfectly, the structure of the strip section being maintained. Consequently, as was not to be expected immediately, the nonwoven strip section also remains adhering firmly to the nonwoven ribbon section when the latter is rolled up to form the rolled blank, even though centrifugal forces act on it and especially on its free unsealed end. As a result of the firm sealing bond between the strip section and the nonwoven ribbon, the thermoplastic material preserves its smooth surface, when the expanded tampon filled with absorbed body fluid is removed from the body cavity again by means of the withdrawal cord. The lower friction relative to the wall of the body cavity, achieved by means of the strip section, contributes to ensuring that the fibre structure of the expanded tampon preserves its form corresponding approximately to the tampon blank.

Figure 6:
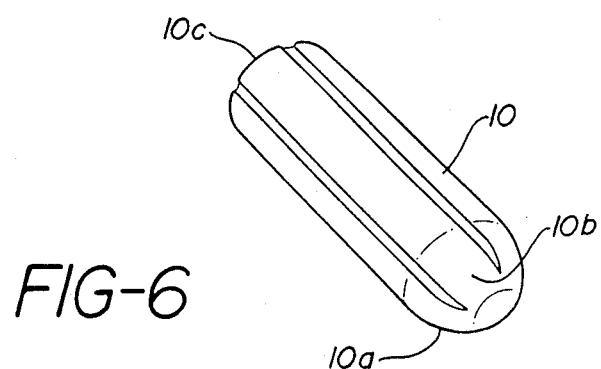
Figure 7:
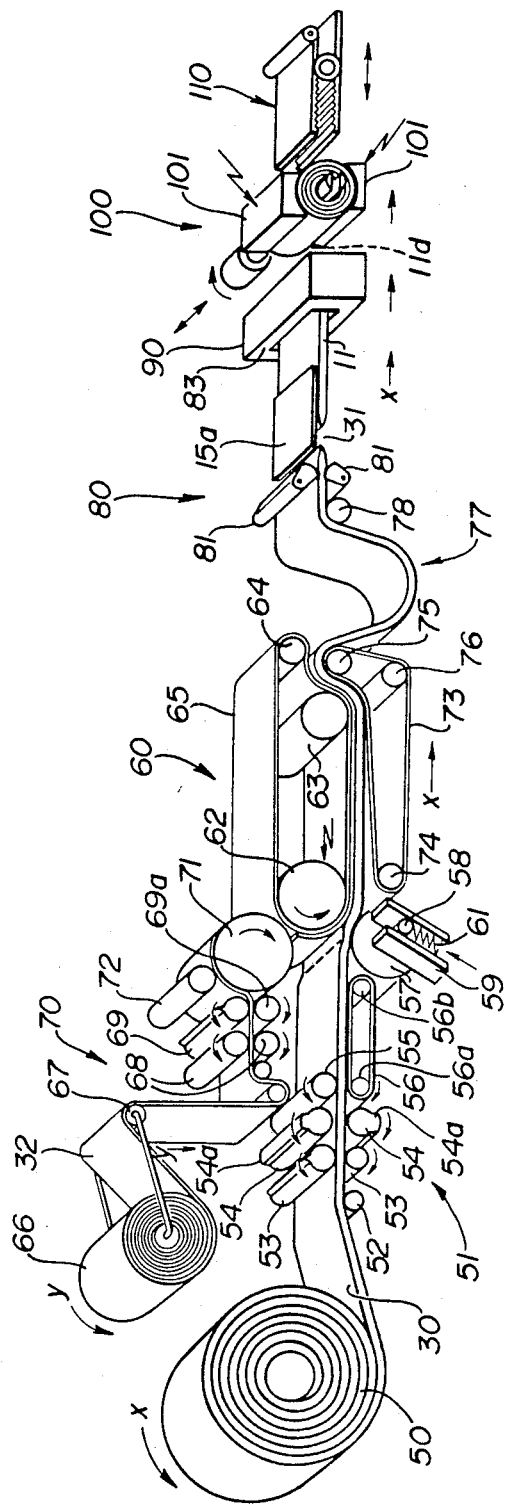

The invention is described in more detail below with reference to the diagrammatic drawing of an exemplary embodiment. In the drawing:

FIGS. 1 to 6 show process steps for producing the tampon according to the invention and FIG. 7 shows, in a diagrammatic view, an apparatus for producing the tampon according to the invention, and shows a modified embodiment of the apparatus in FIG. 7, and FIG. 9 shows a plan view of transport and severing tongs in the gripping position.

FIG. 6 illustrates a tampon 10 for female hygiene, which consists of a section 11, evident in FIG. 3, of specific length of a calendered nonwoven ribbon 30 (FIGS. 1, 2, 7 and 8) composed of randomly laid natural and/or synthetic fibres and having a width approximately corresponding to the length of the tampon 10. This nonwoven ribbon section 11 is essentially rolled up on itself about an axis lying transversely to its longitudinal direction outside the longitudinal centre of the nonwoven ribbon section 11, to form a tampon blank 12 and at the same time it is provided with a withdrawal cord 13. The tampon blank 12 is pressed essentially radially to the winding axis to give the final form of the tampon 10. As a result of the pressure applied, the tampon is provided with press notches arranged distributed over equal circumferential angles. The introduction end 10a of the tampon 10 is designed as a constriction 10b resembling a round dome.

According to the invention, a strip section 15 consisting of liquid-permeable, thermoplastic material is sealed to the part of the nonwoven ribbon section 11 forming the circumferential surface of the tampon 10, with the application of heat and pressure, although this strip section is made longer than the circumference of the tampon blank 12.

FIGS. 2 to 4 show that the thermoplastic strip section 15 is bonded firmly to the nonwoven ribbon 30 by means of weld seams 79 parallel to and at a distance from one another, which form an acute angle with the longitudinal direction of the nonwoven ribbon. The distances between the individual weld seams 79 are such that, between the weld seams, the liquid-permeable material of the strip section 15 rests closely on the nonwoven ribbon material. This guarantees that liquid coming up against the strip section 15 on the circumferential surface of the tampon is immediately absorbed into the interior of the tampon by means of the capillary action of the fibre material of the nonwoven ribbon section 11 located underneath.

The outer end 15a of the strip section 15 extends beyond the outer end 11a of the nonwoven ribbon section 11 and is welded to the outside of part of the strip section 15 sealed to the nonwoven ribbon section 11 with the application of heat and pressure.

It is evident that the thermoplastic liquid-permeable strip section 15 is narrower than the width of the nonwoven ribbon section 11, but is flush with the longitudinal edge 11b of the non-woven ribbon section 11 forming the withdrawal end 10c i of the tampon 10. The longitudinal edge 11c of the non-woven ribbon section 11 forming the introduction end 10a of the tampon 10 projects beyond the associated edge 15c of the liquid-permeable, thermoplastic strip section 15 over a width approximately corresponding to the height of the dome-like constriction 10b of the tampon 10 at the introduction end 10a. The liquid-permeable strip is composed at least predominantly of thermoplastic nonwoven fibre material preferably produced from a bi-component fibre, the components of which consist, for example, of a polyester core and a high-pressure polyethylene sheathing. It is particularly appropriate if the high-pressure polyethylene has a lower melting point than the polyester. Since the free outer end 15a of the thermoplastic strip section 15 is welded to the outside of that length section of the strip section 15 which is sealed to the nonwoven ribbon section 11, the strip section 15 forms, in the circumferential direction of the tampon blank 12, a wrapping which is joined firmly to this and the outside diameter of which corresponds to that of the tampon blank 12. Since the wrapping is welded firmly to the fibre material of the nonwoven ribbon 30, a high capillary action of the fibre material through the wrapping is ensured so that, after being pressed in a press provided with jaws arranged in the form of a star, such as that described, for example, in German Patent Specification 1,491,161, the tampon 10 has a suction capacity and absorbency which are equal to those of a corresponding tampon without a wrapping, but is protected against fibres becoming detached and against them loosing their spiral form.

The process for producing the above-described tampon consists of the following steps which are described below with reference to FIGS. 1 to 6:

According FIG. 1, a calendered nonwoven ribbon 30, consisting of randomly laid natural and/or synthetic fibres and having a width corresponding to the length of the tampon 10, is supplied continuously and is weakened, for example as a result of perforation, by means of a so-called weak points 31, between sections 11 of a length necessary for producing the tampon 10, transversely to its longitudinal direction. This weakening is also achieved as a result of a stretching of the nonwoven ribbon 30, so that a thinning of the nonwoven ribbon 30 or a reduction in its cross-section, but not severing of the nonwoven ribbon 30, occurs in the stretch zone or at the weak point 31. The nonwoven ribbon is moved further continuously in the direction of the arrow x. Approximately at the same time, a continuously supplied strip 32 of thermoplastic, liquid-permeable nonwoven material is severed, each time, into a strip section 15, the length of which exceeds the circumference of the tampon blank 12 shown in FIG. 5. The liquid-permeable, thermoplastic strip section 15 is then sealed to the outside of a region of the nonwoven ribbon 30 at the rear in the direction of movement x of the nonwoven ribbon 30 and located in front of a weak point 31, with the application of heat and pressure along parallel weld seams 79 extending obliquely relative to the longitudinal direction of the nonwoven ribbon 30. The arrangement of the strip section 15 on the top side of the nonwoven ribbon 30 is such that the outer end 15a (FIG. 3), at the rear in the direction of movement x of the nonwoven ribbon 30, of the strip section 15 extends freely, that is to say unsealed, beyond the weak point 31 of the nonwoven ribbon 30. The nonwoven ribbon 30 is then severed at the weak point 31, so that the nonwoven ribbon section 11 is obtained.

After that the nonwoven ribbon section 11 is essentially rolled up on itself, to give a tampon blank 12 shown in FIG. 5, about an axis extending transversely to its longitudinal direction and represented in FIG. 3 by a winding mandrel 33, this taking place according to FIG. 4. The nonwoven ribbon section 11 is rolled up in such a way that one end 11a of the outer layer of the rolled-up nonwoven ribbon section 11 overlaps the other end 11d (See FIGS. 3 and 5) of the layer of rolled-up nonwoven ribbon section 11 located underneath in the circumferential direction of the tampon blank 12. As as result, a more uniform material distribution and consequently an essentially cylindrical form of the tampon blank 12 is achieved on the outer circumference of the latter.

As is evident from FIG. 5, the length of the thermoplastic, liquid-permeable strip section 15 is such that the latter completely surrounds the circumference of the tampon blank 12 over the intended width, the free or unsealed end 15a initially still projecting on the outside. The winding operation is now concluded when this free, unsealed end 15a of the strip section 15 is sealed, with the application of heat and pressure, to the part, adjacent to the outer end of the nonwoven ribbon section 11 in the circumferential direction of the tampon blank 12, of the thermoplastic strip section 15 sealed to the nonwoven ribbon section 11. Since the high-pressure polyethylene surfaces of the melted fibres come to rest on one another during this time, the sealing pressure does not need to be as high as in the previous sealing of the strip section 15 to the nonwoven ribbon 30 to achieve a good seal.

According to FIG. 3, before the winding operation, the withdrawal cord 13 is placed round the nonwoven section 11 transversely to the longitudinal direction of the latter and, if appropriate, is subsequently knotted at its free ends. The finished tampon blank 12 is then delivered to a press which, according to German Patent Specification 1,491,161, consists of press jaws arranged in the form of a star and in which the tampon blank 12 is pressed essentially radially to give the final form of the tampon 10 shown in FIG. 6. The introduction end 10a of the tampon is then shaped in the form of a dome-like constriction 10b, to make it easier to introduce the tampon into the body cavity. For the present process it is not important where and how the withdrawal cord 13 is applied in detail.

It goes without saying that the length of the strip section 15 depends on the final diameter of the tampon blank 12. The length of the freely projecting unsealed end 15a of the strip section 15 also depends on this and is usually between 10 and 50 mm.

It is evident from FIGS. 2 to 6 that the outside of the nonwoven ribbon 30 is covered with the liquid-permeable, thermoplastic strip section 15 over a width which extends from the longitudinal edge 11b of the nonwoven ribbon 30, forming the withdrawal end 10c of the tampon 10, only into the vicinity of the longitudinal edge 11c of the nonwoven ribbon section 11, forming the introduction end 10a of the tampon 10. The longitudinal edge 11c of the nonwoven ribbon 30 not covered by the thermoplastic strip section 15 is made so wide that, after the tampon blank 12 has been pressed to give the final form of the tampon 10, the strip section 15 can be shaped to form the dome-like constriction 10b of the introduction end 10a of the tampon 10. This guarantees at the same time that the introduction end 10a free of the strip section 15 is subjected directly to the body fluid to be absorbed and consequently the tampon expands without delay and can thereby exercise its full absorbency and perform its complete protective function for the user. Because of its low coefficient of friction, the thermoplastic, nonwoven material ensures the comfort of easy, gentle introduction of the tampon into the body cavit and protection against fibres becoming detached when the tampon is introduced into or removed from the body cavity. Furthermore, because of the sliding capacity, substantially greater in comparison with the nonwoven material of the strip section 15 on the circumference of the tampon, any tendency for the tampon to lose its spiral form when removed from the body cavity after use is essentially counteracted.

FIG. 7 shows an apparatus for producing the tampon according to the invention, using the process described above. The left-hand part of the drawing shows a nonwoven ribbon 30 which is supplied continuously to a weakening station 51 in the direction of movement x from a stock roll 50. The weakening station 51, preceded by a supporting roller 52, consists, in the direction of movement of the nonwoven ribbon 30, of a pair of perforating and clamping rollers 53 and a pair of stretching rollers 54. Since the perforating and clamping rollers 53 retain the nonwoven ribbon in front of the stretching rollers 54 at the moment of stretching, and since the stretching rollers 54 cause by means of their stretching jaws 54a an acceleration in the direction of transport x of the nonwoven ribbon grasped by them, the nonwoven ribbon 30 is thinned or reduced in cross-section in the zone between the perforating and clamping rollers 53 and the stretching rollers 54, so that the weak point 31 is obtained. The weakening station 51 is followed, on the top side of the path of movement of the nonwoven ribbon, by a transport roller 55 and, on the underside, by an endless carrying belt 56 which is guided round a front driving and tensioning roller 56a, located directly under the transport roller 55, and a further deflecting roller 56b.

A sealing station 60 consists of a pressure roller 57 which is located under the path of movement of the nonwoven ribbon 30 and the axle 58 of which is mounted at both ends in a guide 59 movable up and down and is supported at each end on a compression spring 61. The spring-loaded pressure roller 57 is movable by means of the guide 59 in the direction of a sealing roller 62 intermittently, for example by means of a control cam not shown. The sealing roller 62 can be heated in a suitable way, for example by means of electrical resistance heating, and can be driven in an anticlockwise direction. Furthermore, a larger and a smaller deflecting roller 63 and 64 are assigned to the sealing roller 62. The smaller deflecting roller 64 is arranged at a higher level behind the deflecting roller 63 of larger diameter, in the direction of movement x of the nonwoven ribbon 30. An endless sealing tape 65 is laid round the sealing roller 62 and the two deflecting rollers 60 and 64 and is made of a material which is heat-resistant relative to the temperature of the sealing roller 62, but is capable of transmitting the heat of the sealing roller 62 to the outside of the endless sealing tape 65. The preferred materials used for the sealing tape 65 are silicone rubber or strip steel which guarantee good heat transmission from the sealing roller 62 to the thermoplastic strip section 15 and a long life. The surface of the sealing tape 65 can be profiled according to a desired sealing pattern, so that the welding points between the nonwoven ribbon 30 and the strip section 15 are provided at a distance from one another (weld seams 79 in FIG. 3).

It is evident that there is in front of the sealing station 60, above the nonwoven ribbon 30 and the weakening station 51, a stock roll 66 for the continuous strip 32 of nonwoven, liquid-permeable and thermoplastic fibre material, which is supplied to a cutting station 70 via a sprung deflecting roller 67.

The cutting station 70 consists of a pair of transport rollers 68 arranged above and below the strip 32 and driven in opposite directions and of a pair cutting rollers 69, 69a which are arranged after them and which are likewise driven in opposite directions and of which the blade roller 69 is provided on a substantial part of a circumferential line with cutting edges for largely severing the strip 15. The circumferential speed of the transport rollers 68 and cutting rollers 69, 69a approximately corresponds to half the transport speed of the nonwoven ribbon 30, so that the strip 32 can be drawn off continuously from the stock roll 66, in the direction of the arrow y, at the speed corresponding to the length of the strip section 15 of nonwoven material to be applied.

The cutting rollers 69 cut through the strip 32 in the transverse direction substantially, but not completely, so that the leading strip section 15 formed as a result of cutting is still joined to the following strip by means of some small so-called webs.

The cutting station 70 is followed by a vacuum roller 71, the constructive design of which is shown in more detail in FIG. 8 and which is described in more detail below in connection with the description of the modified embodiment shown in this Figure. An acceleration roller 72 of smaller diameter is assigned to the vacuum roller 71 on the top side and serves to press the nonwoven material against the vacuum roller 71. The circumferential speed of the vacuum roller 71 and of the acceleration roller 72 corresponds to the transport speed of the nonwoven ribbon 30. The vacuum roller 71 is provided with holes on its circumferential surface, the hollow interior of the vacuum roller being connected to a vacuum source which can be connected and disconnected (not shown). Consequently, the strip section 15 coming from the cutting station 70 can be sucked against the circumference of the vacuum roller 71 and, in the stretched position, carried in a clockwise direction into the nip formed by the vacuum roller 71 with the acceleration roller 72. As soon as the front end of the strip section 15 passes into the nip between the acceleration roller 72 and the vacuum roller 71, the strip section 15 is accelerated to double the speed, in particular the speed of the nonwoven ribbon, and is consequently torn off completely from the following nonwoven strip 32 in the region of the cut made in the cutting station 70.

The vacuum roller 71 now carries the strip section 15 attached to its circumference by suction to the nip which the vacuum roller 71 forms with the endless sealing tape 65 on the sealing roller 62. Since the vacuum roller 71 touches the endless sealing tape 65 obliquely above and in front of the sealing roller 62, and at this point the vacuum is shut off in the direction of rotation of the vacuum roller 71, as described in more detail below, the thermoplastic strip section 15 is taken up at the earliest possible moment by the sealing roller 62 and the heated endless sealing tape 65 as a result of adhesion and is heated. Consequently, when carried along further through the nip between the sealing roller 62 and the vacuum roller 71, the strip section 15 is preheated by the endless sealing tape 65 when it strikes the surface of the nonwoven ribbon 30, so that the melt fibres of the strip section 15 melt in the region of the nip between the pressure roller 57 and the sealing roller 62, and, because of the correct pressure and temperature setting, an intimate bond with the fibres on the surface of the nonwoven ribbon is produced.

In the region of the upper sealing tape 65, there is again, underneath the path of movement of the nonwoven ribbon 30, an endless conveyor belt 73 guided round a deflecting roller 74 which is at the front in the direction of movement x of the nonwoven ribbon and which is arranged behind the pressure roller 57 and at a short distance underneath the nonwoven ribbon 30. The conveyor belt 73 presses the nonwoven ribbon, together with the strip section 15 of nonwoven material sealed to it, against the larger deflecting roller 63 of the sealing tape 65, since a deflecting roller 75 of the lower endless conveyor belt 73 is pressed into the nip between the larger deflecting roller 63 and the smaller deflecting roller 64 of the sealing tape 65 located behind it, but at a higher level. The conveyor belt 73 is guided downwards approximately transversely to the nonwoven ribbon 30 round a further deflecting or tensioning roller 76. The endless tape and belt 65 and 73 are driven continuously in a clockwise or anti-clockwise direction, so that the nonwoven ribbon, with the thermoplastic strip section 15 sealed to it, is constantly transported further. As a result of the deflection described, it is guaranteed that the nonwoven ribbon section 11, with the strip section sealed to it, will be detached perfectly from the sealing tape 65. If appropriate, the deflecting rollers 63, 64 can be cooled.

FIG. 2 shows the nonwoven ribbon 30 after the strip section 15 has been sealed to the particular rear end 11a of a nonwoven ribbon section 11. It is evident that the rear end 15a of the strip section 15 extends beyond the weak point 31 of the nonwoven ribbon 30 up to the following nonwoven ribbon section 11, but is not sealed to the nonwoven ribbon 30. To guarantee this, the guide 59 with the spring-loaded pressure roller 57 is designed so as to be movable up and down in the direction of and counter to the sealing roller 62 and can be controlled so that, in the operating state illustrated in FIG. 7, the pressure roller 57 is moved away downwards out of contact with the nonwoven ribbon 30. As a result, the nonwoven ribbon 30 sags between the conveyor belts 56 and 73 and is supported on the conveyor belt 73, the deflecting roller 74 of which is lower in relation to the path of movement of the nonwoven ribbon 30, when the later is pressed against the sealing roller 62 by means of the pressure roller 57. In the end region of the endless sealing tape 65, its temperature is so low that there is no possibility of softening or melting of the melt fibres of the free, unsealed end 15a of the strip section 15, and this end continues to rest unsealed on the nonwoven ribbon 30.

The endless tape 65 and endless belt 73 are followed by a compensating or relief region 77 for the nonwoven ribbon 30 with the strip sections 15 welded to it at length intervals, and in this region the nonwoven ribbon sags between the two abovementioned endless conveyor belts and a guide roller 78. This compensating region separates the preceding continuous working process from the following intermittent process.

The guide roller 78 is followed by a part of a nonwoven ribbon-severing device 80 consisting of a pair of clamping jaws 81 which are respectively attached so as to be pivotable to and fro to the top side and underside of the path of movement of the nonwoven ribbon 30. The clamping jaws 81 respectively clamp the nonwoven ribbon 30, behind the rear, unsealed end 15a of the strip section 15, intermittently to the nonwoven ribbon section 11 located in front of it, in order, as described below, to make it possible to sever the nonwoven ribbon section 11 from the nonwoven ribbon 30.

The clamping jaws 81 are followed by a withdrawal cord-attaching and -knotting device 90 which can be designed according to German Patent Specification 1,491,160 and which is therefore not shown in any more detail. It is sufficient to point out that the withdrawal cord 13 is laid round the nonwoven ribbon section 11 by means of this device, and its free ends are knotted together when severing and transport tongs 110 have drawn forward the nonwoven ribbon section 11, as described below. The withdrawal cord 13 hangs down (not shown) from the longitudinal edge 11b of the nonwoven ribbon section 11 forming the withdrawal end 10c of the tampon 10. The nonwoven ribbon section 11 is guided through an orifice 83 in the device 90.

There is subsequently provided a winding station 100 which serves for producing the tampon blank 12 and which is followed by the severing and transport tongs 110 which, when the winding mandrel 33 is retracted, are movable to and fro through the orifice 83 in the device 90 at the height of the path of movement of the nonwoven ribbon 30 in and counter to the direction of movement of the latter, and which are described in German Patent Specification 915,382. These severing and transport tongs 110 grasp the front free end 11d of the nonwoven ribbon 30 and, with the latter being severed at the weak point 31, pull it behind the clamping jaws 81 clamping the nonwoven ribbon 30, into the effective range of the withdrawal cord-attaching and -knotting device 90 and the winding station 100, in which the nonwoven ribbon section 11 formed is maintained in the stretched position. At this moment, the fork-shaped winding mandrel 33 is moved forwards axially, from its position retracted out of the path of movement of the nonwoven ribbon 30, with its fork prongs above and below the nonwoven ribbon section 11, so that the nonwoven ribbon section 11 is located in the fork gap and the winding mandrel still projects slightly beyond the width of the nonwoven ribbon section 11. The winding mandrel 33 engages over the nonwoven ribbon section 11 in a cross-sectional region located behind the longitudinal centre of the nonwoven ribbon section 11 in the direction of movement x, so that the rear end 11a of the nonwoven ribbon section 11 (FIG. 3) overlaps the front end 11d of the latter when rolled up in the circumferential direction of the tampon blank 12.

Spreading jaws 101, preferably heatable by means of electrical resistance heating, are arranged parallel to the winding axis on diametrically opposite sides of the winding mandrel 33 and can be pressed radially relative to the winding axis against the tampon blank 12 by means of a control device not shown. The spreading jaws 101 are heated to a temperature sufficient to melt together the superimposed melt fibres of the freely projecting, unsealed end 15a of the strip section 15 and thereby provide a closed wrapping, solid in the circumferential direction and consisting of nonwoven material. Thus, the temperature and pressing force of the spreading jaws 101 can be made lower than the temperature and pressing forces of the sealing roller 62.

The further transport of the tampon blank 12 to a tampon press can be carried out by means of a device such as that described in German Patent Specification 1,938,942. The press can be designed according to German Patent Specification 1,491,161. The dome-like constriction 106 at the introduction end 10a of the tampon 10 is produced, after pressing, by means of a heated forming die such as that described in German Patent Specification 1,491,200.

FIG. 8 shows a diagrammatic representation of a modified embodiment of the apparatus for producing the tampon in FIG. 6, parts unchanged in respect of the embodiment in FIG. 7 bearing the same reference symbols.

A pressure roller 200 is located immediately after the weakening station 51. In contrast to the embodiment in FIG. 7, there is no provision for the sealing tape 65 in FIG. 8. Here, only a sealing roller 201, described in more detail below, is provided for sealing purposes.

Located at the height of the sealing roller 201 and underneath the path of movement of the nonwoven ribbon 30 is a belt conveyor 202 consisting of a plurality of front drive pulleys 203 and rear deflecting pulleys 204 which each carry an endless guide belt 205.

The guide belts 205 are supported on the upper side by a supporting roller 206, opposite which is located, on the top side of the path of movement of the nonwoven ribbon 30, a pressure roller 207 of substantially larger diameter. The supporting roller 206 and the pressure roller 207 come up against one another with a clamping effect, so that the nonwoven ribbon 30 is retained when the nonwoven ribbon section 11 located behind in the direction of movement is drawn out of the transport system by means of the transport and severing tongs 110 located behind the belt conveyor 202. The upper side of the guide belts 205 has assigned to it a deflecting roller 208, from which the upper side of the guide belt 205 is deflected obliquely downwards towards the deflecting pulleys 204.

Located above the path of movement of the nonwoven ribbon 30 is a guide device 209 which likewise consists of several deflecting pulleys 210, 211 which are offset axially and at a distance relative to one another and on which endless belts 212 are again arranged so as to be axially offset, these being arranged respectively above the guide belts 205 of the lower belt conveyor 202. The front deflecting pulleys 210 of the guide device 209 are located close behind the pressure roller 207, whilst the rear deflecting pulleys 211 are arranged above the rear deflecting pulleys 204 of the belt conveyor 202. The lower side of the endless belt 212 of the guide device 209 has assigned to it, in the vicinity of the deflecting pulleys 211, a deflecting roller 227, from which the lower side is directed obliquely upwards to the deflecting pulleys 211. Consequently, the upper side of the guide belts 205 and the lower side of the endless belts 212 form behind the deflecting rollers 208 and 227, in the direction of movement of the nonwoven ribbon 30, an opening slit 228, into which the severing and transport tongs 110 can move, through the orifice 83 in the withdrawal cord-attaching and -knotting device 90, to grasp the particular front end of the nonwoven ribbon 30 intermittently.

The rear deflecting pulleys 211 and 204 of the upper guide device 209 or of the lower belt conveyor 202 are each provided, over 180°, with guide segments 213 and 214 which project radially outwards and run in synchronism with one another and which carry or guide the nonwoven ribbon 30 when the transport and severing tongs 110 move, counter to the direction of transport x of the nonwoven ribbon 30, in the direction of the slit 228 between the deflecting pulleys 211 and 204, in order to grasp the front end of the nonwoven ribbon 30 and draw the latter, at a speed higher than the transport speed of the nonwoven ribbon, into the effective range of the withdrawal cord-attaching and -knotting device 90 and the winding station 100. Since the pressure roller 207 with the supporting roller 206 is located at a distance greater than the length of a nonwoven ribbon section 11 from the slit 228 for the transport and severing tongs 110 to grasp the front end of the nonwoven ribbon 30, each weak point 31 of the nonwoven ribbon 30 is located behind the pressure roller 207 and the supporting roller 206, so that the transport and severing tongs 110 pull away the section of the nonwoven ribbon 30 extending up to the weak point 31 behind the pressure roller 207 and tear it off at the weak point 31. After this separation of the nonwoven ribbon section 11, the latter is guided by means of the transport tongs 110 into the region of the withdrawal cord-attaching and -knotting device 90 and the winding station 100. Whilst the withdrawal cord 13 can be attached and knotted in the way described in conjunction with FIG. 7, the winding station 100 is likewise equipped with a winding mandrel 33 which is movable axially to and fro and which can be driven in the direction of rotation. However, in the winding station 100 according to FIG. 8, the spreading jaws 215, 216 for sealing the free projecting end 15a of the strip section 15 to the part of the strip section 15 fastened to the tampon blank 12 are of different design.

The lower and upper spreading jaws 215, 216 are associated at a radial distance from the winding mandrel 33, and preferably only the lower spreading jaw 215 can be heated, this extending in the third quadrant of a circle over an angle of approximately 190° to 280°. A heatable sealing element 218 is arranged so that it can move to and fro relative to the winding mandrel 33 through a perforation 217 in the lower spreading jaw 215 and is intended for sealing the hitherto unsealed rear end 15a of the strip section 15 to part of the strip section 15 fastened to the circumference of the tampon blank 12. Since the end face 218a of the sealing element 218 is narrow, it is possible to weld the outer edge of the free end 15a of the strip section 15 only along a circumferential line to the material of the same strip section 15 fastened to the circumference of the tampon blank 12.

FIG. 9 shows a plan view of the severing and transport tongs 110, the bit of which consists of three pairs of prongs 110a which, in the gripping position shown, engage into interspaces corresponding to the prongs and located between the guide segments 213 and 214 of the guide device 209 and the belt conveyor 202 respectively. The lower side of the endless belts 212 and the upper side of the guide belts 205 are arranged at a distance from one another, through which the nonwoven ribbon 30 is not compressed, but merely carried along without any substantial press function, so that it is immediateley guaranteed that the nonwoven ribbon section 11 will be drawn out between the abovementioned sides by means of the severing and transport tongs 110 and that the following nonwoven ribbon 30 will be torn off at the weak point 31 of the latter.

In the embodiment according to FIG. 8, the same devices as in FIG. 7 are provided for supplying, cutting to length and transferring the thermoplastic strip section 15 to the vacuum roller 71. In FIG. 8, only the design of the vacuum roller 71 is evident in greater detail, in as much as there is located in the interior of the vacuum roller 71 a slide 219 which is fixed and which is provided over its circumference of approximately 180° with lateral suction orifices 220 which allow a suction effect via smaller suction orifices 221 connected to them and located in the circumferential wall of the vacuum roller 71.

FIG. 8 shows in an enlarged representation the special design of the sealing roller 201 which makes it possible, without an endless sealing tape, to carry out sealing only over a part circumference of the sealing roller 201 by means of heatable sealing elements 223, 224 which are arranged diametrically opposite one another on a basic body 222 and which are profiled according to the welding or sealing pattern. The circumferential length of the sealing elements 223 and 224 corresponds in each case exactly to the length of a strip section 15 which is to be sealed to the nonwoven ribbon section 11. Two unheated insulating elements 225, 226 are fastened to the basic body 222 and are offset 90° relative to the sealing elements 223, 224 located diametrically opposite one another. The circumferential arcs of the insulating elements 225, 226 have the same radius as the outer surfaces of the sealing elements 223, 224, so that a circumferential surface composed of circular sectors of the same radius is obtained. The arrangement of the insulating elements 225, 226 ensures that the free or unsealed end 15a of the thermoplastic strip sections 15, which projects beyond the sealing elements 223 or 224 counter to the direction of rotation of the sealing roller 201, will always come to rest on one of the insulating elements 225, 226 and will consequently not be sealed against the nonwoven ribbon 30.

To guarantee that the strip sections 15 composed of thermoplastic nonwoven material come to rest exactly on the respective sealing elements 223 and 224, the cutting rollers 69 are rotated approximately at half the circumferential speed of the vacuum roller 71, as already mentioned further above. The cutting rollers 69 cut through the strip 32 substantially, but not completely, so that on both sides of this cut the unwoven strip of material 32 continues to remain joined by means of webs of material (not shown) in a similar way to a perforation. The following acceleration roller 72 is driven at a rotational speed corresponding to the circumferential speed of the vacuum roller 71 and consequently to the transport speed of the nonwoven ribbon 30. When the front end of the nonwoven strip of material 32 comes into the effective range of the acceleration roller 72, the section 15 of the strip of material 32 located in front of the cut is torn off and accelerated to the speed of the nonwoven ribbon, so that the individual strip sections 15 are guided, at the correct distance from one another, up to the end of one of the two sealing elements 223, 224 which is at the front in the direction of rotation.

The strip of material 32 located behind the tear-off point is always smoothed and stretched in the direction of transport as a result of the suction effect of the vacuum roller 71. Because of the extremely low mass of the severed strip section 15, the latter is accelerated abruptly to the speed of the nonwoven ribbon, so that the strip section 15 can always be positioned exactly on the vacuum roller 71.

As is evident from FIG. 8, a slit 219a of the slide 219 of the vacuum roller 71 ends shortly before the nip which the vacuum roller 71 forms with the sealing roller 201. In the region of the nip between the vacuum roller 71 and sealing roller 201, the thermoplastic strip section 15 is heated to such an extent that it becomes ductile and tacky and consequently adheres to the sealing roller 201 and is carried along free of slip by the latter, but it is guaranteed that the strip section 15 will be received and carried along reliably by the nonwoven ribbon section 11 after sealing.

It is therefore evident from the above description that the apparatus according to the FIG. 8 allows continuous transport of the nonwoven ribbon 30 up to the withdrawal cord-attaching and -knotting device 90 or the winding station 100, and, of the devices transporting the nonwoven ribbon 30, only the severing and transport tongs 100 execute a to-and-fro movement, whilst all the other devices constantly rotate in one direction. It is also evident that, by means of the devices described, not only is a high production speed achieved such as is necessary for mass production, but also economical mass production of a substantially improved tampon for female hygiene can be obtained as a result, whilst ensuring a quality which remains high.

I claim:

1. A substantially cylindrical tampon for female hygiene having an axial length, outer circumference and a withdrawal cord extending from a first axial end, comprising:
    (a) a nonwoven ribbon composed of randomly laid fibres, said ribbon having a width approximately the same as the length of the tampon, said ribbon extending spirally about an axis parallel to the direction of said width substantially in the form of a cylinder having an outer surface, and said spirally wound ribbon being compressed radially;
    (b) a strip section of liquid permeable at least partially thermoplastic material bonded intermittently to said ribbon by heat sealing said strip in face to face contact along said outer surface to form an outer layer of said tampon, which layer is compressed radially with said ribbon; and
    (c) a first end of said strip section extending beyond an end of said ribbon and welded to said outer layer to make said outer layer continuous along said outer circumference.

2. A tampon according to claim 1 wherein:
    (a) said strip section has a width less than the width of said ribbon.

3. A tampon according to claim 2 wherein:

(a) said strip section covers said first axial end of said tampon.

4. A tampon according to claim 2 wherein:
(a) a portion of said ribbon extends beyond and uncovered by said strip at a second axial end of said tampon.

5. A tampon according to claim 2 wherein:
(a) an edge of the width of said strip is contiguous with an edge of the width of said ribbon.

6. A tampon according to claim 1 wherein:
(a) the liquid permeable thermoplastic strip section is composed of bi-component fibre.

7. A tampon according to claim 6 wherein:
(a) the bi-component fibre consists of a polyester core and a sheathing of high-pressure polyethylene which has a melting point lower than that of the polyester.

8. A tampon according to claim 1 wherein:
(a) the bond between the strip section and the nonwoven ribbon is provided at equally spaced locations.

9. A tampon according to claim 8 wherein:
(a) the bond locations are in the form of lines.

10. A tampon according to claim 8 wherein:
(a) the bond locations are in the form of spots.

* * * * *